United States Patent
Kim et al.

(10) Patent No.: US 7,906,227 B2
(45) Date of Patent: Mar. 15, 2011

(54) INDENE DERIVATIVE COMPOUND AND ORGANIC LIGHT EMITTING DEVICE COMPRISING THE SAME

(75) Inventors: Myeong-suk Kim, Yongin-si (KR); Dong-woo Shin, Yongin-si (KR); Yu-jin Kim, Yongin-si (KR); Byoung-ki Choi, Yongin-si (KR); Tae-yong Noh, Yongin-si (KR); O-hyun Kwon, Yongin-si (KR); Tae-woo Lee, Yongin-si (KR); Eun-sil Han, Yongin-si (KR); Woon-jung Paek, Yongin-si (KR)

(73) Assignees: Samsung Electronics Co., Ltd., Yeongtong-gu, Suwon-si, Gyeonggi-do (KR); Samsung Mobile Display Co., Ltd., Nongseo-Dong, Giheung-Gu, Yongin, Gyunggi-Do (KR)

( * ) Notice: Subject to any disclaimer, the term of this patent is extended or adjusted under 35 U.S.C. 154(b) by 263 days.

(21) Appl. No.: 12/078,734

(22) Filed: Apr. 3, 2008

(65) Prior Publication Data

US 2009/0098397 A1 Apr. 16, 2009

(30) Foreign Application Priority Data

Oct. 15, 2007 (KR) ........................ 10-2007-0103732

(51) Int. Cl.
*B32B 15/04* (2006.01)
(52) U.S. Cl. ........................ 428/690; 428/457; 568/327
(58) Field of Classification Search ........................ None
See application file for complete search history.

(56) References Cited

U.S. PATENT DOCUMENTS 4,885,211 A   12/1989  Tang et al.
(Continued)

FOREIGN PATENT DOCUMENTS

JP   11-003782   1/1999
JP   11-329734   11/1999

OTHER PUBLICATIONS

Kawamura et.al., 100% phosphorescent quantum efficiency of Ir (III) Complexes, Applied Physics Letters 2005, pp. 071104-1 to 071104-3.*

(Continued)

*Primary Examiner* — D. Lawrence Tarazano
*Assistant Examiner* — Gregory Clark
(74) *Attorney, Agent, or Firm* — Robert E. Bushnell, Esq.

(57) ABSTRACT

Provided are an indene derivative compound represented by Formula 1 below and an organic light emitting device including the same:

$$X-Ar_1-Ar_2-Y \qquad \text{Formula 1}$$

wherein $Ar_1$, $Ar_2$ and X are described in the detailed description, and
Y is represented by one of Formulae 2a to 2d:

Formula 2a

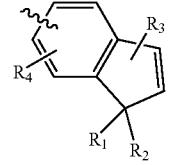

Formula 2b

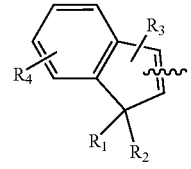

Formula 2c

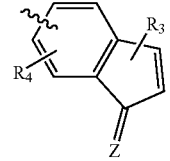

Formula 2d
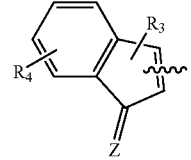

wherein $R_1$ to $R_4$ and Z are described in the detailed description.

An organic light emitting device having improved driving voltage properties, brightness, efficiency and color purity can be prepared by including the indene derivative compound.

17 Claims, 3 Drawing Sheets

U.S. PATENT DOCUMENTS

| | | | |
|---|---|---|---|
| 5,077,142 A | * 12/1991 | Sakon et al. | 428/690 |
| 5,151,629 A | 9/1992 | VanSlyke | |
| 2007/0160870 A1 | * 7/2007 | Yu et al. | 428/690 |

OTHER PUBLICATIONS

Adv. Mater. 1994, 6, No. 9, p. 677 by Yoshiyuki, et al. Entitled *Thermally Stable Multilayered Organic Electroluminescent Devices Using Novel Starburst Molecules, 4,4',4"-Tri(N-Carbazolyl)Triphenylamine (TCTA) and 4,4',4"-Tris(Methylphenylphenyl-Amino) Triphenylamne (M-Mtdata), as Hole-Transport Materials*, published in 1994.

* cited by examiner

INDENE DERIVATIVE COMPOUND AND ORGANIC LIGHT EMITTING DEVICE COMPRISING THE SAME

CLAIM OF PRIORITY

This application makes reference to, incorporates the same herein, and claims all benefits accruing under 35 U.S.C. §119 from an application for earlier filed in the Korean Intellectual Property Office on 15 Oct. 2007 and there duly assigned Serial No. 10-2007-0103732.

BACKGROUND OF THE INVENTION

1. Field of the Invention

The present invention relates to an indene derivative compound and an organic light emitting device including the same, and more particularly, to an indene derivative compound having excellent electrical properties and providing excellent driving voltage properties, high efficiency and high color purity to an organic light emitting device when applied to the organic light emitting device and an organic light emitting device including the indene derivative compound.

2. Description of the Related Art

Organic light emitting devices are active light emitting display devices that emit light by recombination of electrons and holes in a thin layer made of a fluorescent or phosphorescent organic compound (an organic layer) when a current is applied to the organic layer. The organic light emitting devices have advantages such as lightweight, simple constitutional elements, easy fabrication process, superior image quality and wide viewing angle. Furthermore, the organic light emitting devices can accomplish perfect creation of dynamic images and high color purity. The organic light emitting devices also have electrical properties suitable for portable electronic equipment such as low power consumption and low driving voltage.

A multi-layered organic light emitting device using an aluminum quinolinol complex layer and a triphenylamine derivative layer was developed by Eastman Kodak Co. (U.S. Pat. No. 4,885,211), and a wide range of light from ultraviolet lights to infrared lights can be emitted using low-molecular weight materials when an organic emitting layer is formed (U.S. Pat. No. 5,151,629).

Light emitting devices, which are self light emitting display devices, have wide viewing angles, excellent contrast and quick response. Light emitting devices are classified into inorganic light emitting devices using inorganic compounds to form emitting layers and organic light emitting devices (OLED) using organic compounds to form emitting layers. Organic light emitting devices have higher brightness, lower driving voltages and quicker responses than inorganic light emitting devices and can realize multi colors. Thus, organic light emitting devices have been actively studied.

Typically, an organic light emitting device has an anode/organic emitting layer/cathode structure. An organic light emitting device can also have various other structures, such as an anode/hole injection layer/hole transport layer/emitting layer/electron transport layer/electron injection layer/cathode structure or an anode/hole injection layer/hole transport layer/emitting layer/hole blocking layer/electron transport layer/electron injection layer/cathode structure.

Materials that are used in organic light emitting devices can be classified into vacuum deposited materials and solution coated materials according to a method of preparing an organic layer. The vacuum deposited materials may have a vapor pressure of $10^{-6}$ torr or greater at the temperature of 500° C. or less and be low molecular materials having a molecular weight of 1200 or less. The solution coated materials may be highly soluble in solvents to be prepared in solution phase, and include aromatic or heterocycle groups.

Japanese Patent Publication No. 1999-003782 discloses an anthracene substituted with two naphthyl groups which can be used for an light emitting layer or a hole injection layer. However, the organic light emitting device including the anthracene does not have sufficient driving voltage, brightness, efficiency and color purity properties, and thus those properties need to be improved.

SUMMARY OF THE INVENTION

The present invention provides an indene derivative compound capable of improving driving voltage properties, efficiency and color purity of an organic light emitting device and an organic light emitting device including the indene derivative compound.

According to an aspect of the present invention, there is provided an indene derivative compound represented by Formula 1 below:

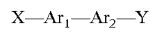

Formula 1 wherein $Ar_1$ is selected from the group consisting of a substituted or unsubstituted $C_5$-$C_{50}$ arylene group, a substituted or unsubstituted $C_5$-$C_{30}$ heteroarylene group, a substituted or unsubstituted $C_5$-$C_{50}$ alkenylene group and a combination of at least two of them which are connected by a single bond, $Ar_2$ is selected from the group consisting of a substituted or unsubstituted $C_5$-$C_{15}$ arylene group, a substituted or unsubstituted $C_5$-$C_{15}$ heteroarylene group, a substituted or unsubstituted $C_5$-$C_{15}$ alkenylene group and a combination of at least two of them which are connected by a single bond, X is selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group, a substituted or unsubstituted $C_3$-$C_{30}$ arylsilane group and a group represented by one of Formulae 2a through 2d, and Y is a group represented by one of Formulae 2a through 2d:

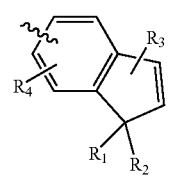

Formula 2a

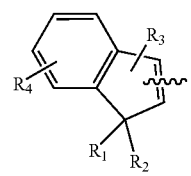

Formula 2b

-continued

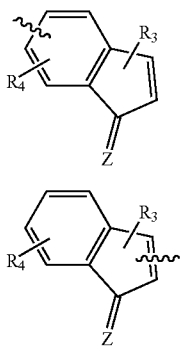

Formula 2c

Formula 2d wherein $R_1$ to $R_4$ are each independently selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group and a substituted or unsubstituted $C_3$-$C_{30}$ arylsilane group, and Z is O or S.

According to another aspect of the present invention, there is provided an organic light emitting device comprising: a first electrode; a second electrode; and at least one organic layer interposed between the first electrode and the second electrode, wherein the organic layer comprises the indene derivative compound according to the present invention.

An organic light emitting device prepared using an indene derivative compound represented by Formula 1 according to the present invention can have improved emitting properties such as excellent driving voltage properties, high efficiency, high brightness and high color purity by forming a thermally stable organic layer.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1A:
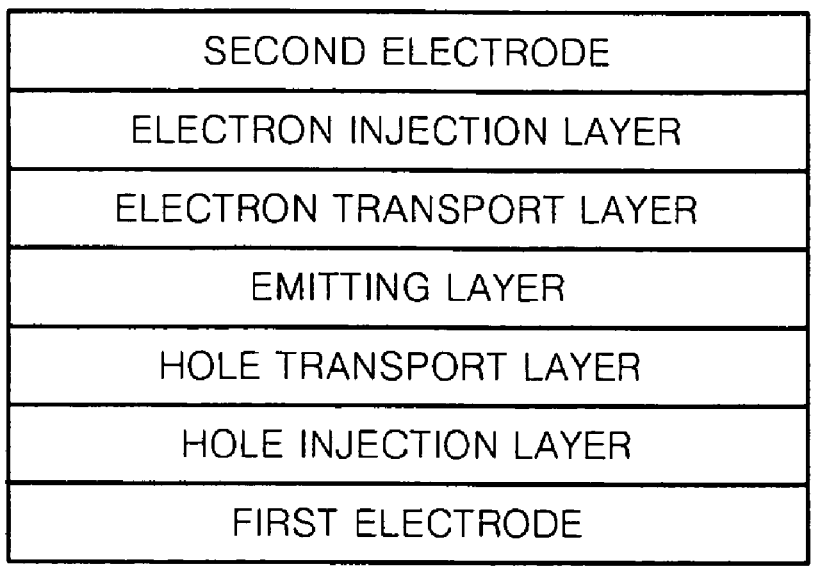
FIGS. 1A through 1C are schematic sectional views of organic light emitting devices according to embodiments of the present invention.

Hereinafter, the present invention will now be described more fully with reference to the accompanying drawings, in which exemplary embodiments of the invention are shown.

An indene derivative compound according to the present invention is represented by Formula 1 below:

$$X\text{—}Ar_1\text{—}Ar_2\text{—}Y \quad \text{Formula 1}$$

wherein $Ar_1$ is selected from the group consisting of a substituted or unsubstituted $C_5$-$C_{50}$ arylene group, a substituted or unsubstituted $C_5$-$C_{30}$ heteroarylene group, a substituted or unsubstituted $C_5$-$C_{50}$ alkenylene group and a combination of at least two of them which are connected by a single bond, $Ar_2$ is selected from the group consisting of a substituted or unsubstituted $C_5$-$C_{15}$ arylene group, a substituted or unsubstituted $C_5$-$C_{15}$ heteroarylene group, a substituted or unsubstituted $C_5$-$C_{15}$ alkenylene group and a combination of at least two of them which are connected by a single bond, X is selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group, a substituted or unsubstituted $C_3$-$C_{30}$ arylsilane group and a group represented by one of Formulae 2a through 2d, and Y is a group represented by one of Formulae 2a through 2d:

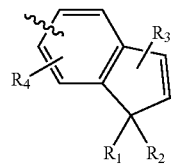

Formula 2a

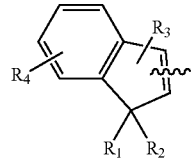

Formula 2b

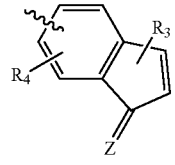

Formula 2c

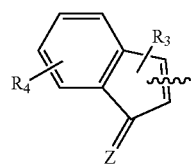

Formula 2d wherein $R_1$ to $R_4$ are each independently selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group and a substituted or unsubstituted $C_3$-$C_{30}$ arylsilane group, and Z is O or S.

Here, the "∼∼∼" shown in Formulae 2a to 2d is a linking group of Formula 1 and Formulae 2a to 2d indicate the formulae below.

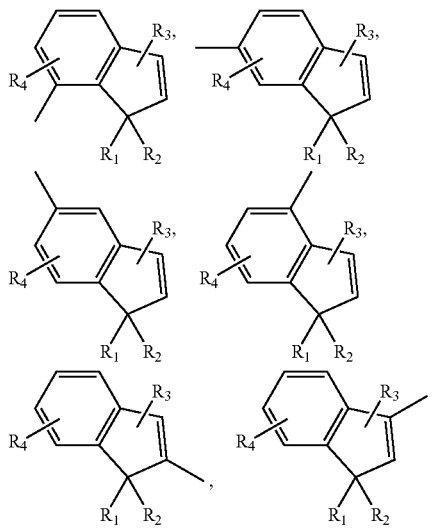

Examples of the unsubstituted alkyl group are a methyl group, an ethyl group, a propyl group, an isobutyl group, a sec-butyl group, a tert-butyl group, a pentyl group, an isoamyl group and a hexyl group, and at least one of hydrogen atoms of the alkyl group may be substituted with a substituent.

Examples of the unsubstituted cycloalkyl group are a cyclohexyl group and a cyclopentyl group, and at least one of hydrogen atoms of the cycloalkyl group may be substituted with a substituent.

Examples of the unsubstituted alkoxy group are a methoxy group, an ethoxy group, a phenyloxy group, a cyclohexyloxy group, a naphthyloxy group, an isopropyloxy group and a diphenyloxy group, and at least one of hydrogen atoms of the alkoxy group may be substituted with a substituent.

The aryl group indicates a carbocyclic aromatic system having at least one aromatic ring which can be attached to each other or fused with each other using a pendent method. Examples of the unsubstituted aryl group are a phenyl group, an ethylphenyl group, an ethylbiphenyl group, an o-, m- and p-fluorophenyl group, a dichlorophenyl group, a dicyanophenyl group, a trifluoromethoxyphenyl group, o-, m-, or p-tolyl group, o-, m- or p-cumenyl group, a mesityl group, a phenoxyphenyl group, a (α,α-dimethylbenzen)phenyl group, a (N,N'-dimethyl)aminophenyl group, a (N,N'-diphenyl)aminophenyl group, a pentalenyl group, an indenyl group, a naphthyl group, a methylnaphthyl group, an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, an ovalenyl group and a carbazolyl group. At least one of hydrogen atoms of the aryl group may be substituted with a substituent.

The unsubstituted aralkyl group is an aryl group in which hydrogen atoms are substituted with a short-chain alkyl group such as a methyl group, an ethyl group and a propyl group. Examples of the aralkyl group are a benzyl group and a phenylethyl group. At least one of hydrogen atoms of the aralkyl group may be substituted with a substituent.

The unsubstituted heteroaryl group indicates a monovalent monocyclic or bicyclic aromatic organic compound having 6 to 30 membered rings including C and 1 to 3 hetero atoms selected from the group consisting of N, O, P and S. At least one of hydrogen atoms of the heteroaryl group may be substituted with a substituent. Examples of the heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazynyl group, a carbazolyl group and an indolyl group.

Examples of the unsubstituted arylene group are a phenylene group and a biphenylene group, and at least one of hydrogen atoms of the arylene group may be substituted with a substituent.

The unsubstituted heteroarylene group indicates a bivalent monocyclic or bicyclic aromatic organic compound having 6 to 30 membered rings including C and 1 to 3 hetero atoms selected from the group consisting of N, O, P and S. At least one of hydrogen atoms of the heteroarylene group may be substituted with a substituent.

The unsubstituted arylamino group may be represented by —Ar—N(Q1)(Q2), wherein Q1 and Q2 are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group. The unsubstituted arylamino group may be a diphenyl amino group, or the like.

The unsubstituted arylsilane group may be represented by —Ar—Si(Q3)(Q4)(Q5), wherein Q3, Q4 and Q5 are each independently a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group or a substituted or unsubstituted $C_5$-$C_{30}$ heterocycloalkyl group.

The "substituted" used herein indicates that a compound is substituted with an arbitrary substituent. Examples of the substituent are —F; —Cl; —Br; —CN; —NO$_2$; —OH; a $C_1$-$C_{50}$ alkyl group which is unsubstituted or substituted with —F, —Cl, —Br, —CN, —NO$_2$ or —OH; a $C_1$-$C_{50}$ alkoxy group which is unsubstituted or substituted with —F, —Cl, —Br, —CN, —NO$_2$ or —OH; a $C_6$-$C_{50}$ aryl group which is unsubstituted or substituted with a $C_1$-$C_{50}$ alkyl group, a $C_1$-$C_{50}$ alkoxy group, —F, —Cl, —Br, —CN, —NO$_2$ or —OH; a $C_2$-$C_{50}$ heteroaryl group which is unsubstituted or substituted with a $C_1$-$C_{50}$ alkyl group, a $C_1$-$C_{50}$ alkoxy group, —F, —Cl, —Br, —CN, —NO$_2$ or —OH; a $C_5$-$C_{50}$ cycloalkyl group which is unsubstituted or substituted with a $C_1$-$C_{50}$ alkyl group, a $C_1$-$C_{50}$ alkoxy group, —F, —Cl, —Br, —CN, —NO$_2$ or —OH; a $C_5$-$C_{50}$ heterocycloalkyl group which is unsubstituted or substituted with a $C_1$-$C_{50}$ alkyl group, a $C_1$-$C_{50}$ alkoxy group, —F, —Cl, —Br, —CN, —NO$_2$ or —OH and a group represented by —N(Q6)(Q7). Here, Q6 and Q7 are each independently a hydrogen atom; a $C_1$-$C_{50}$ alkyl group; or a $C_6$-$C_{50}$ aryl group substituted with a $C_1$-$C_{50}$ alkyl group.

The "derivatives" used herein indicates one of the compounds listed above in which at least one of hydrogen atoms is substituted with the substituent.

The substituent may be a methyl group, a methoxy group, a phenyl group, a tolyl group, a naphthyl group, a pyrenyl group, a phenanthrenyl group, a fluorenyl group, an imidazolinyl group, an indolyl group, a quinolinyl group, a diphenyl amino group, a 2,3-di-p-tolyl aminophenyl group and a triphenylsilyl group.

The $Ar_1$ may be

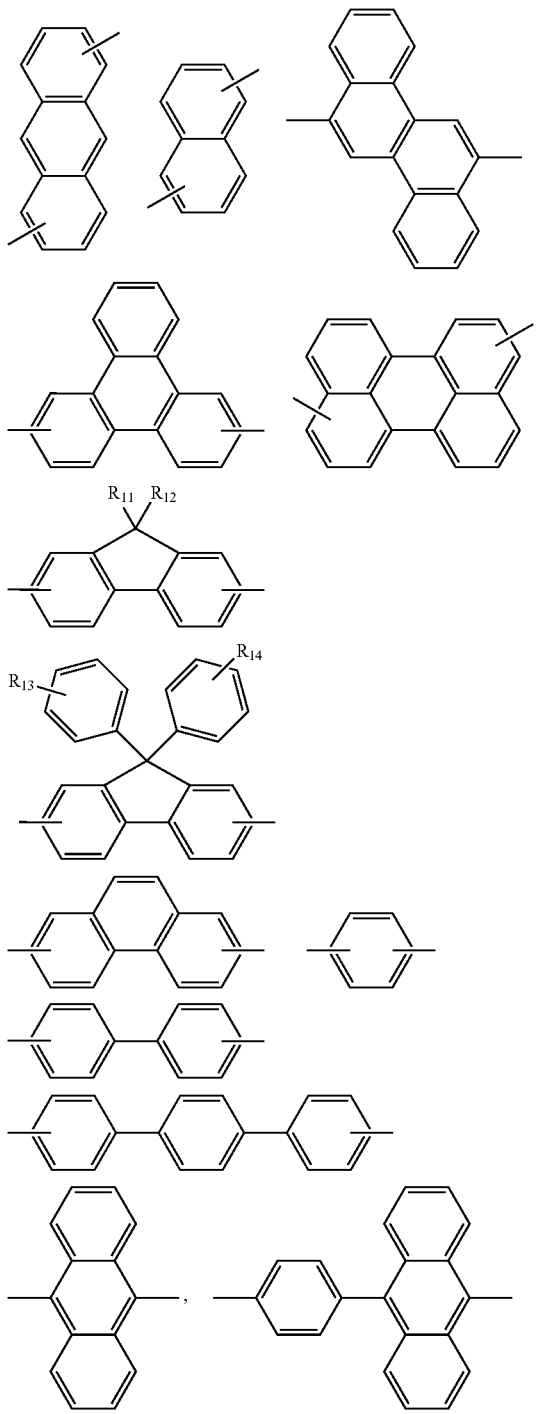

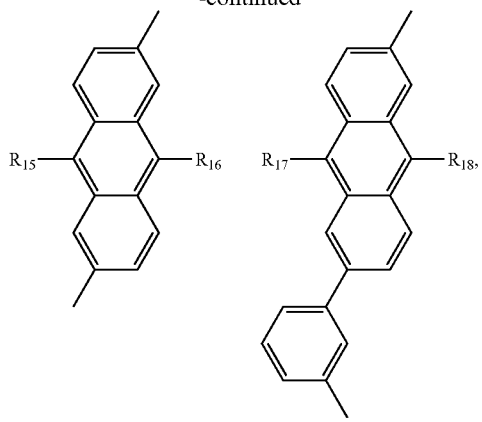

or the like.

Here, $R_{11}$, $R_{12}$, $R_{13}$, $R_{14}$, $R_{15}$, $R_{16}$, $R_{17}$ and $R_{18}$ are each independently selected from the group consisting of a hydrogen atom, a substituted or unsubstituted $C_1$-$C_{20}$ alkyl group, a substituted or unsubstituted $C_6$-$C_{30}$ aryl group, a substituted or unsubstituted $C_2$-$C_{30}$ heteroaryl group, a substituted or unsubstituted $C_5$-$C_{20}$ cycloalkyl group and a substituted or unsubstituted $C_5$-$C_{30}$ heterocycloalkyl group.

The $Ar_1$ provides a main emitting region and thermal stability to the indene derivative compound of the present invention.

The $Ar_2$ may be

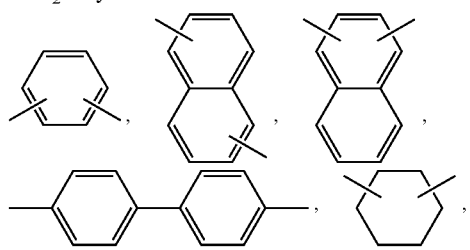

or the like. Here, the $Ar_2$ improves stability of the compound and provides properties of short wavelength due to existence of linking nodes.

The compound of Formula 2 improves thermal stability and photochemical stability of the compound of Formula 1.

In particular, the $R_1$ to $R_4$ and X are each independently a hydrogen atom, a $C_1$-$C_{50}$ alkyl group, a $C_1$-$C_{50}$ alkoxy group, a phenyl group, a biphenyl group, a pentalenyl group, an indenyl group, a naphthyl group, a biphenylenyl group, an anthracenyl group, an azulenyl group, a heptalenyl group, an acenaphthylenyl group, a phenalenyl group, a fluorenyl group, a methylanthryl group, a phenanthryl group, a triphenylene group, a pyrenyl group, a chrysenyl group, an ethylchrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a fluorenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxyranyl group, a pyrrolidinyl group, a pyrazolidinyl group, an imidazolidinyl group, a piperidinyl group, a piperazinyl group, a morpholinyl group, a di($C_6$-$C_{50}$ aryl)amino group, a tri($C_6$-$C_{50}$ aryl)silyl group and derivatives thereof.

X may be a group represented by Formula 2.

The $R_1$ to $R_4$ and X improve film processability by improving solubility and amorphous properties of the indene derivative compound of Formula 1.

The indene derivative compound of Formula 1 may be represented by Formulae 3 to 24 below.

Formula 3

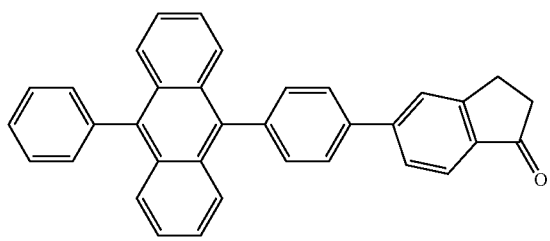

Formula 4

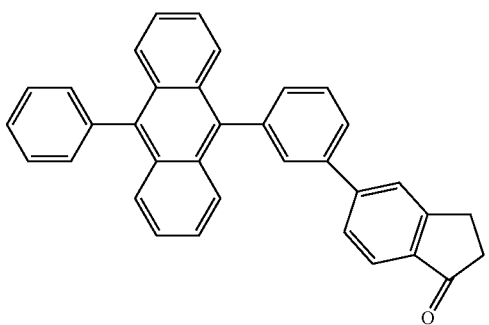

Formula 5

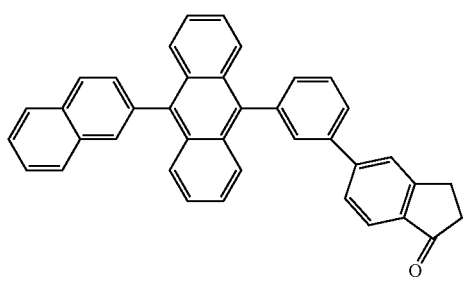

Formula 6

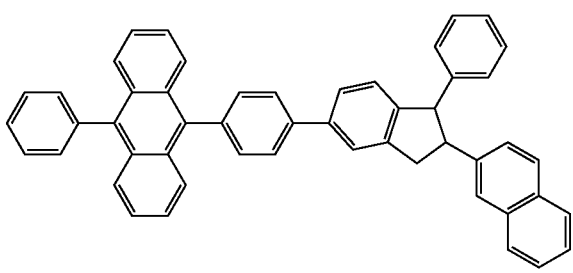

Formula 7

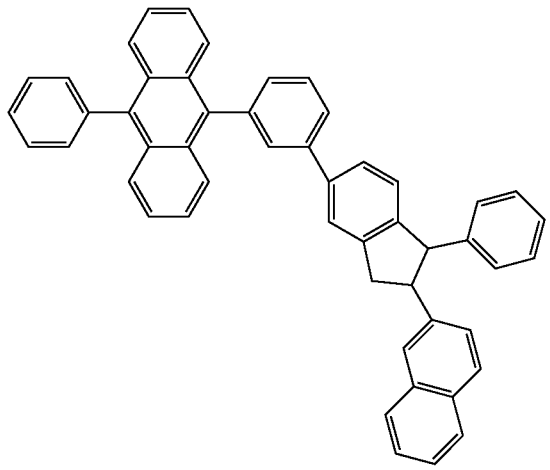

Formula 8

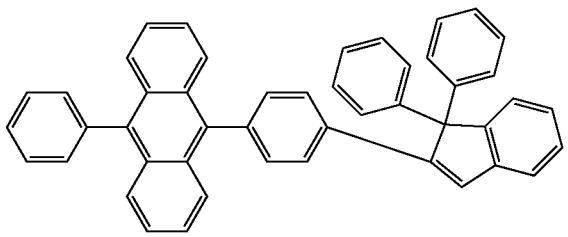

Formula 9

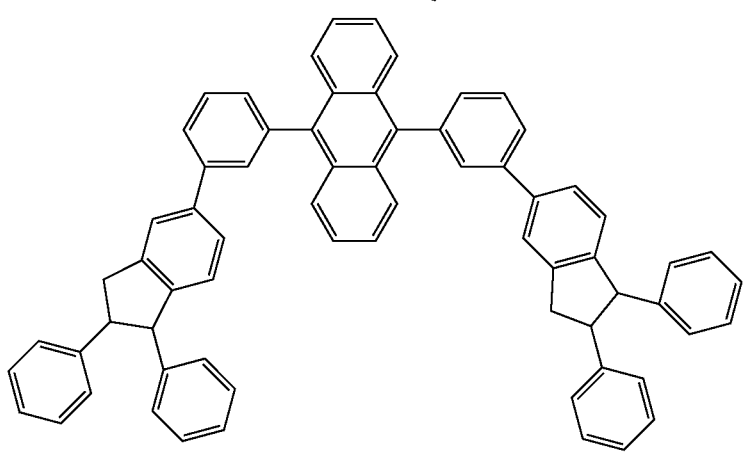

-continued
Formula 10
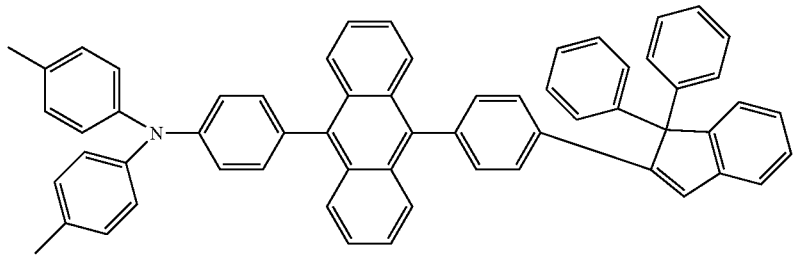
Formula 11
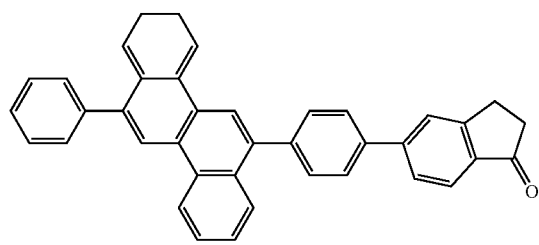
Formula 12
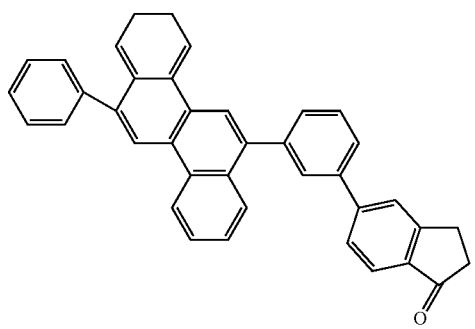
Formula 13
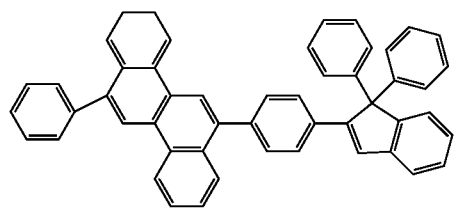
Formula 14
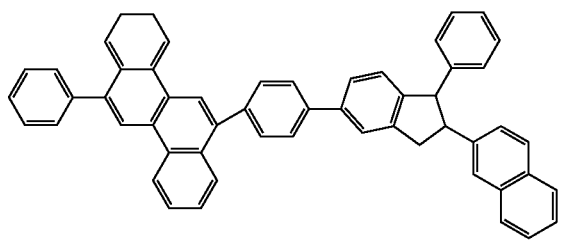
Formula 15
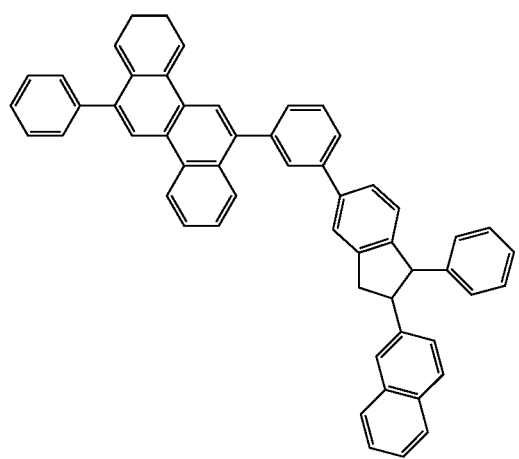
Formula 16
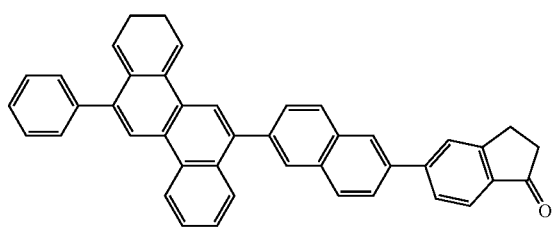

-continued
Formula 17
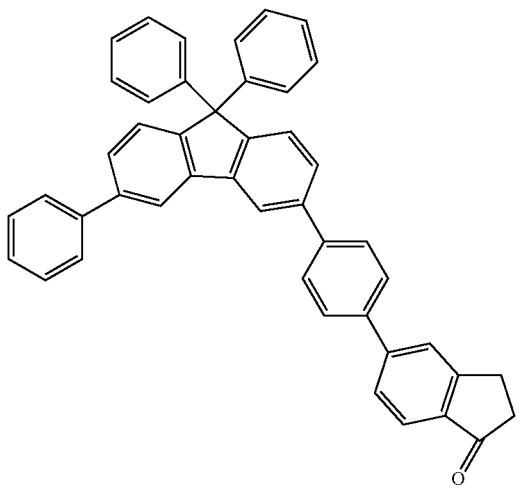
Formula 18
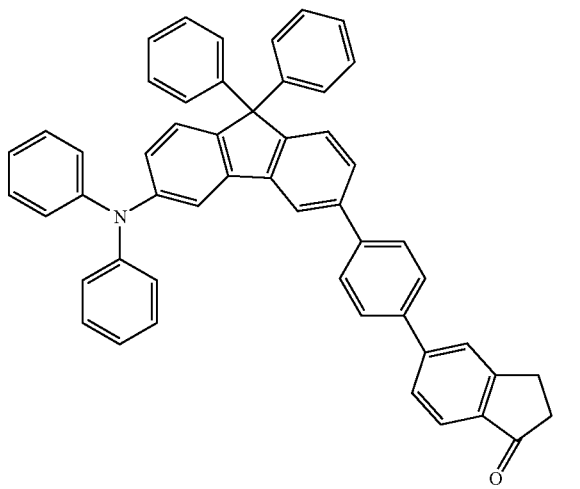
Formula 19
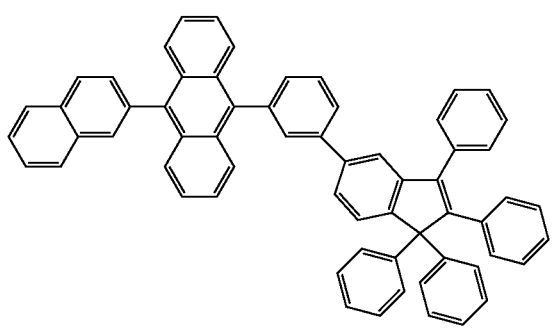
Formula 20
Formula 21
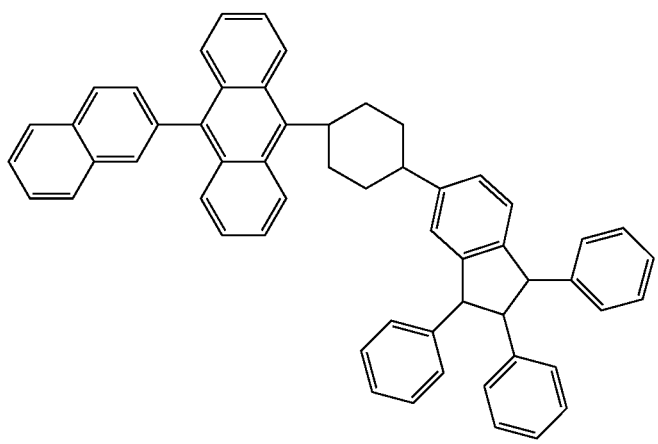
Formula 22
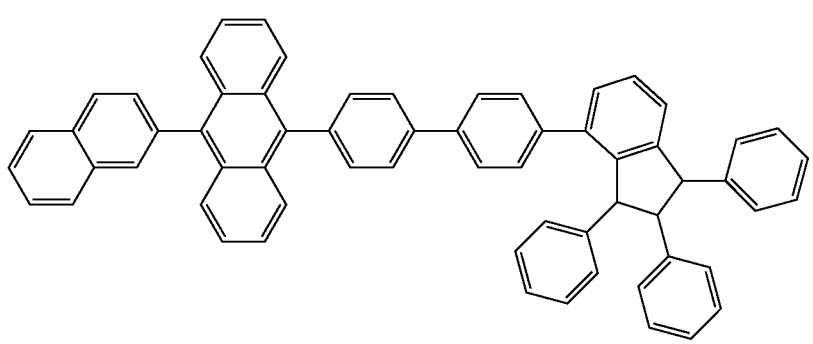

Formula 23

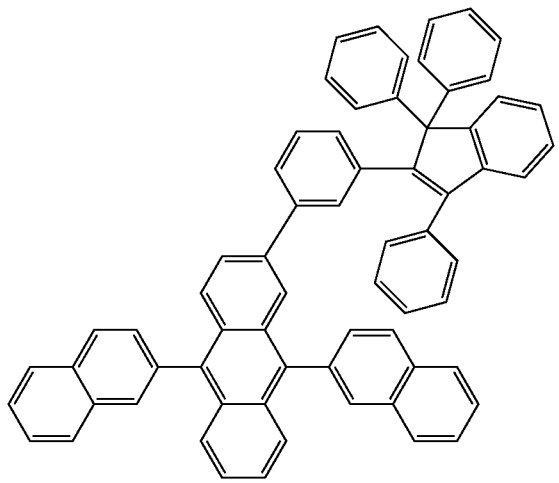

Formula 24

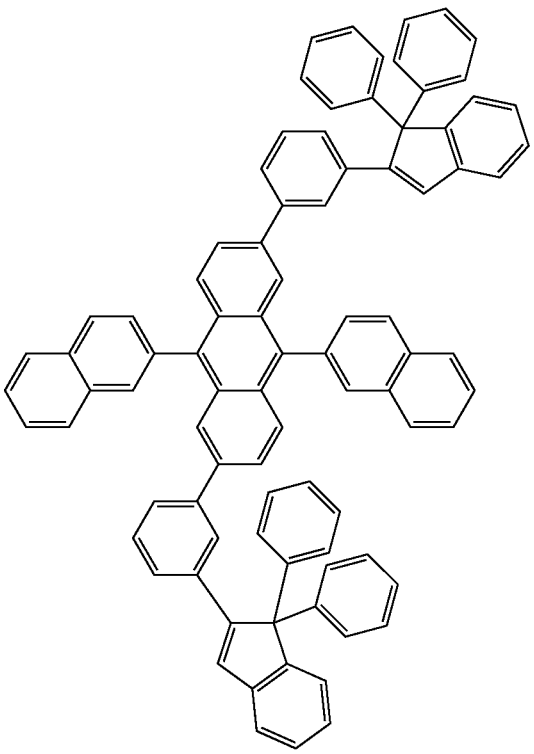

The indene derivative compound of Formula 1 according to the present invention may be synthesized using a method commonly used in the art, and detailed process is shown in reaction schemes below.

According to an embodiment of the present invention, there is provides an organic light emitting device including: a first electrode; a second electrode; and at least one organic layer interposed between the first electrode and the second electrode, wherein the organic layer includes at an indene derivative compound represented by Formula 1 according to the present invention. The indene derivative compound of Formula 1 in the organic light emitting device according to the present invention may be one of the compounds represented by Formulae 3 to 24.

The organic layer may be formed using wet spinning such as spin coating, inkjet printing and spray printing or thermal transfer, but the method is not limited thereto. The organic light emitting device including the indene derivative compound of Formula 1 may be suitably used as a material for a hole injection layer, a hole transport layer, an electron blocking layer, a hole blocking layer, an electron transport layer or an electron injection layer, or a material for a host or dopant of an emitting layer. The emitting layer may further include emitting materials other than the compounds according to the present invention.

Figure 2:
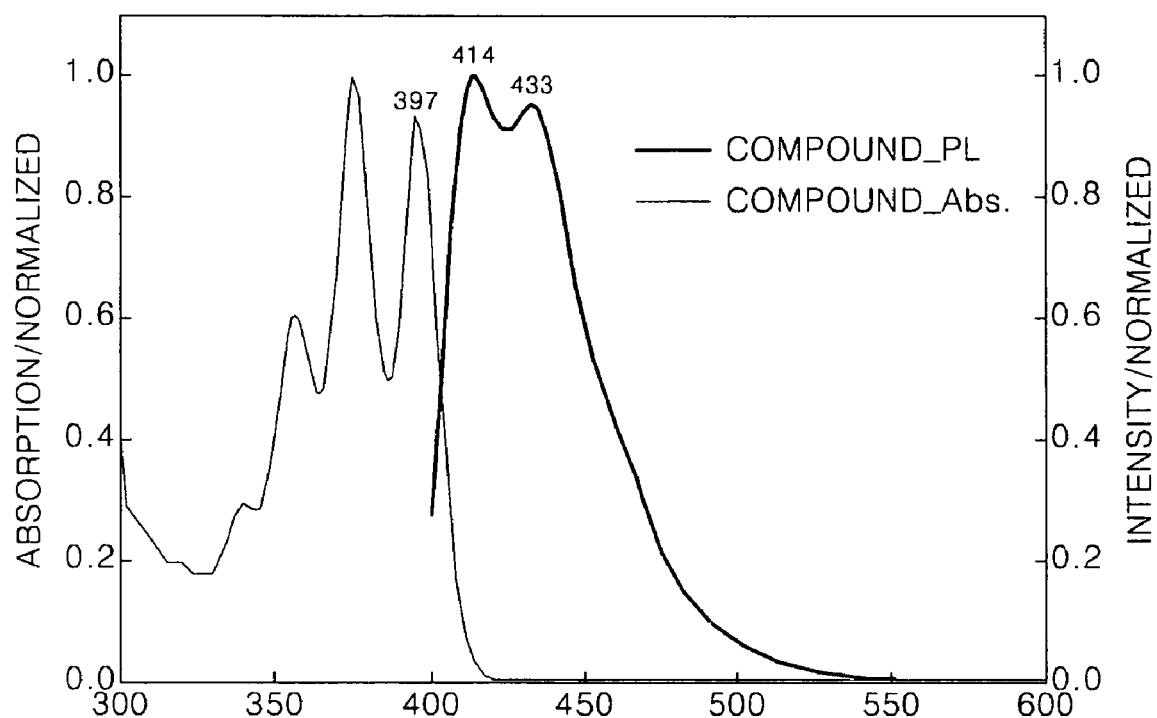
FIG. 2 is a graph illustrating an ultraviolet (UV) spectrum and photoluminescece (PL) spectrum of an indene derivative compound according to an embodiment of the present invention.

FIG. 2 is a graph illustrating an ultraviolet (UV) spectrum and photoluminescece (PL) spectrum of a solution of a compound represented by Formula 3 according to an embodiment of the present invention.

The organic light emitting device according to the present invention may have various structures. The organic light emitting device may further include at least one layer selected from the group consisting of a hole injection layer, a hole transport layer, a hole blocking layer, an electron blocking layer, an electron transport layer and an electron injection layer between the first electrode and the second electrode.

Figure 1B:
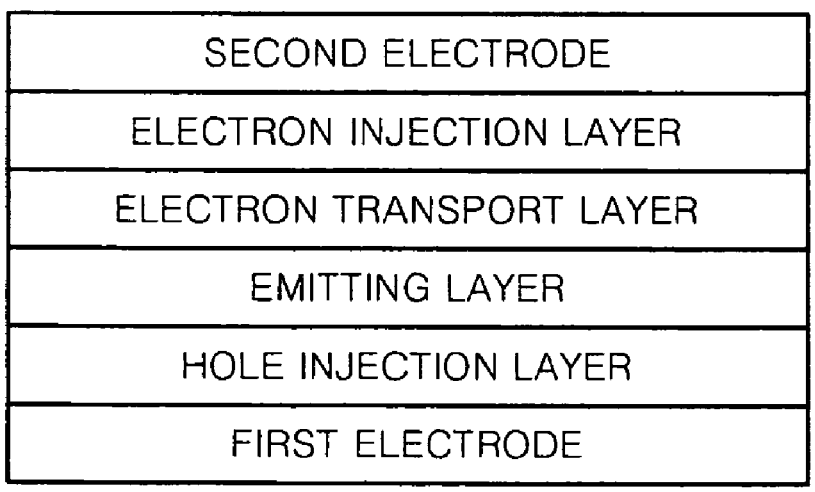
Figure 1C:
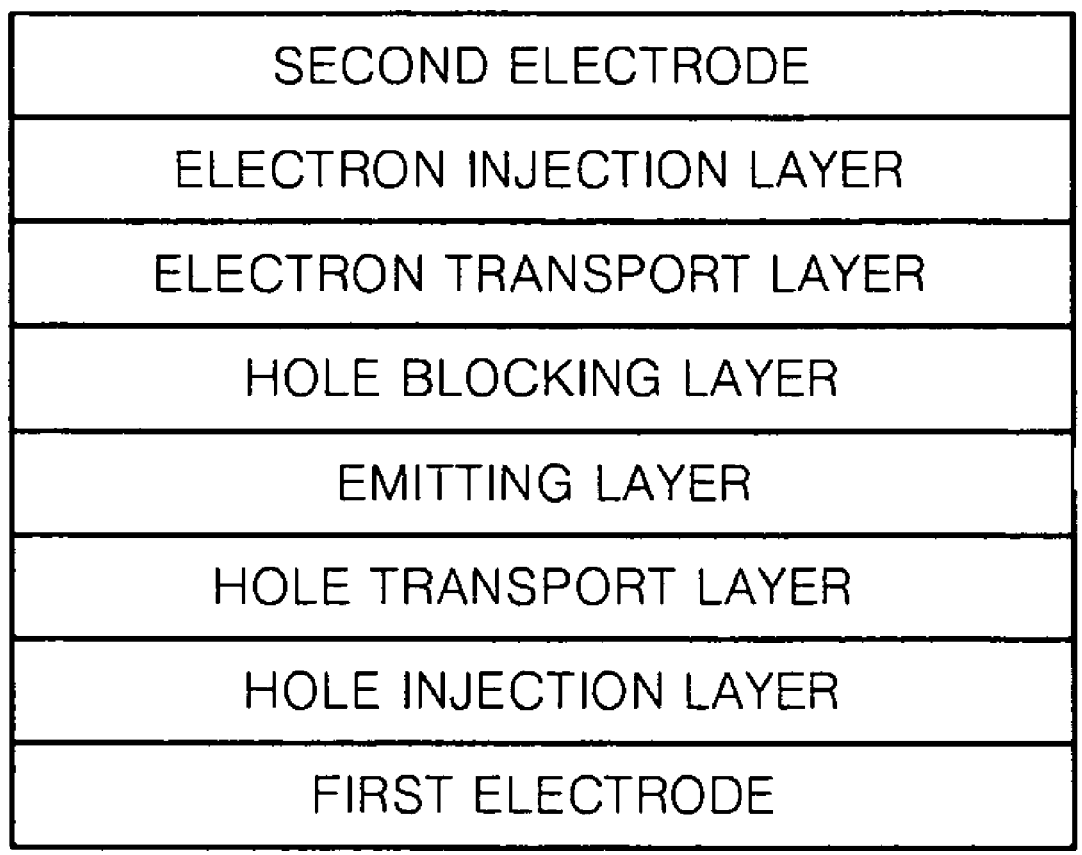

In more particular, examples of the structures of the organic light emitting device according to the present invention are shown in FIGS. 1A to 1C. The organic light emitting device of FIG. 1A has a structure of first electrode/hole injection layer/emitting layer/electron transport layer/electron injection layer/second electrode and the organic light emitting device of FIG. 1B has a structure of first electrode/hole injection layer/hole transport layer/emitting layer/electron transport layer/electron injection layer/second electrode. In addition the organic light emitting device of FIG. 1C has a structure of first electrode/hole injection layer/hole transport layer/emitting layer/hole blocking layer/electron transport layer/electron injection layer/second electrode. Here, at least one layer selected from the group consisting of the electron injection layer, the electron transport layer, the hole blocking layer, the emitting layer, the hole injection layer and the hole transport layer may include a compound according to the present invention.

The organic layer of the organic light emitting device according to the present invention may further include a phosphorescent or fluorescent dopant for red, green, blue or white color. The phosphorescent dopant may be an organic metal compound including at least one element selected from the group consisting of Ir, Pt, Os, Ti, Zr, Hf, Eu, Tb and Tm.

The indene derivative compound according to the present invention which is an organic emitting material having high color purity, excellent color stability and thermal stability can be applied to cellular phones, MP3 players, PDAs, digital cameras, devices for automobiles, display equipped in televisions, or the like, and also used as electronic materials such as organic conductive materials and materials for solar cells.

Hereinafter, a method of preparing an organic light emitting device according to the present invention will be described with reference to FIG. 1C.

First, a first electrode is formed on a substrate, for example, by depositing or sputtering a high work-function material. The first electrode can be an anode. The substrate, which can be any substrate that is used in conventional organic light-emitting devices, may be a glass substrate or a transparent plastic substrate with excellent mechanical strength, thermal stability, transparency, surface smoothness, ease of treatment, and waterproof. The material that is used to form the first electrode can be ITO, IZO, $SnO_2$, ZnO, or any transparent material which has high conductivity.

Then, a hole injection layer (HIL) can be formed on the first electrode by vacuum deposition, spin coating, casting, langmuir Blodgett (LB), or the like.

When the hole injection layer is formed by vacuum deposition, deposition conditions may vary according to a compound that is used to form the hole injection layer, and the structure and thermal properties of the hole injection layer to be formed. In general, however, conditions for vacuum deposition may include a deposition temperature of 100 to 500° C., a pressure of $10^{-8}$ torr to $10^{-3}$ torr, a deposition speed of 0.01 to 100 Å/sec, and a layer thickness of 10 Å to 5 µm.

When the hole injection layer is formed by spin coating, coating conditions may vary according to a compound that is used to form the hole injection layer, and the structure and thermal properties of the hole injection layer to be formed. In general, however, conditions for spin coating may include a coating speed of 2000 to 5000 rpm and a heat-treatment temperature of about 80 to 200° C. to remove a solvent after coating.

The material that is used to form the hole injection layer may be a compound represented by Formula 1 or 2. Alternatively, the material may be a known material such as a phthalocyanine compound, such as a copperphthalocyanine disclosed in U.S. Pat. No. 4,356,429; a star-burst type amine derivative, such as TCTA, m-MTDATA, and m-MTDAPB, disclosed in Advanced Material, 6, p. 677 (1994); or a soluble and conductive polymer such as polyaniline/dodecylbenzenesulfonic acid (Pani/DBSA); poly(3,4-ethylenedioxythiophene)/poly(4-styrenesulfonate (PEDOT/PSS): polyaniline/camphor sulfonic acid (Pani/CSA); and (polyaniline)/poly(4-styrenesulfonate) (PANI/PSS).

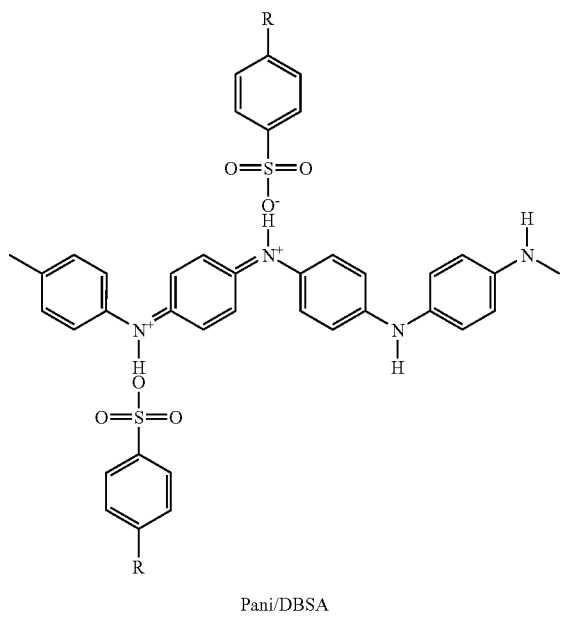

Pani/DBSA

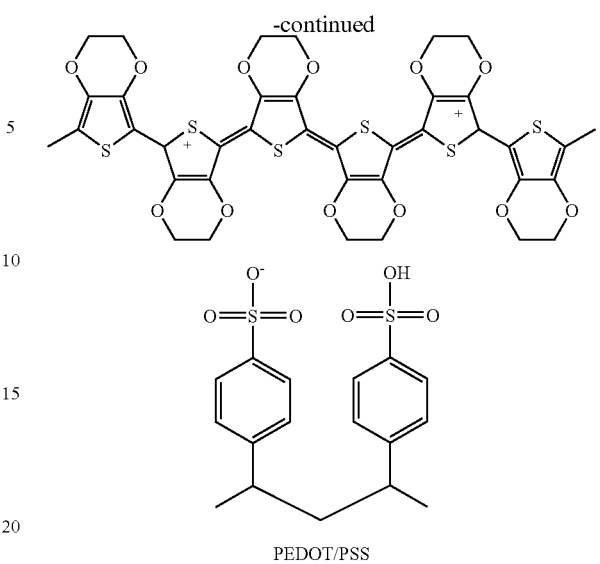

PEDOT/PSS

The thickness of the HIL may be in the range of about 100 Å to 10000 Å, and preferably, in the range of 100 Å to 1000 Å. When the thickness of the HIL is less than 100 Å, the hole injecting ability of the HIL may be reduced. On the other hand, when the thickness of the HIL is greater than 10000 Å, a driving voltage of the device can be increased.

Then, a hole transport layer (HTL) can be formed on the HIL by vacuum deposition, spin coating, casting, LB, or the like. When the HTL is formed by vacuum deposition or spin coating, the conditions for deposition and coating are similar to those for the formation of the HIL, although conditions for the deposition and coating may vary according to the material that is used to form the HTL.

The HTL can be formed of the compound of Formula 1 described above. The HTL may be formed of any material that is conventionally used to form an HTL. For example, the HTL can be formed of a carbazole derivative, such as N-phenylcarbazole and polyvinylcarbazole; and a typical amine derivative having an aromatic condensation ring such as N,N'-bis(3-methylphenyl)-N,N'-diphenyl-[1,1-biphenyl]-4, 4'-diamine (TPD) and N,N'-di(naphthalene-1-yl)-N,N'-diphenyl benzydine (α-NPD).

The thickness of the HTL may be in the range of about 50 to 1000 Å, and preferably, 100 to 600 Å. When the thickness of the HTL is less than 50 Å, a hole transporting ability of the HTL may be reduced. On the other hand, when the thickness of the HTL is greater than 1000 Å, the driving voltage of the device may increase.

Then, an emissive layer (EML) can be formed on the HTL by vacuum deposition, spin coating, casting, LB, or the like. When the EML is formed by vacuum deposition or spin coating, the conditions for deposition and coating are similar to those for the formation of the HIL, although the conditions for deposition and coating may vary according to the material that is used to form the EML.

The EML may be formed of the organic emitting compound having the structure of Formula 1 according to the present invention as described above. Here, an organic semiconductor such as pentacene, polythiophene and tetrathiafulvalene may be used with the organic emitting compound.

Meanwhile, the organic emitting compound of Formula 1 can be used with an appropriate host material that is known in the art. The host material may be, for example, Alq3, 4,4'-N, N'-dicarbazole-biphenyl (CBP) or poly(n-vinylcarbazole (PVK).

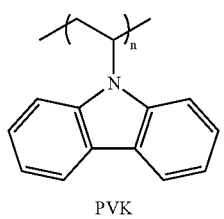

PVK

Meanwhile, various dopants other than the compound according to the present invention may be used as a material that is used to form an emitting layer. For example, IDE102 and IDE105 obtained from Idemitsu Co., C545T obtained from Hiyasibara Co., and the like may be used as a fluorescent dopant, and a red phosphorescent dopant PtOEP and RD 61 obtained from UDC Co., a green phosphorescent dopant Ir(PPy)$_3$ (PPy=2-phenylpyridine) and a blue phosphorescent dopant F2Irpic can be used as a phosphorescent dopant.

The concentration of the dopant is not limited, but is conventionally in the range of 0.01 to 15 parts by weight based on 100 parts by weight of a host.

The thickness of the EML may be in the range of about 100 to 1000 Å, and preferably, in the range of 200 to 600 Å. When the thickness of the EML is less than 100 Å, the emissive ability of the EML may be reduced. On the other hand, when the thickness of the EML is greater than 1000 Å, the driving voltage of the device may increase.

A hole blocking layer (HBL) can be formed on the HTL by vacuum deposition, spin coating, casting, LB, or the like, to prevent diffusion of triplet excitons or holes into an electron transport layer when the phosphorescent dopant is used to form the EML. When the HBL is formed by vacuum deposition or spin coating, the conditions for deposition and coating are similar to those for the formation of the HIL, although the conditions for deposition and coating may vary according to the material that is used to form the HBL. The HBL may be formed of, for example, an oxadiazole derivative, a triazole derivative, a phenanthroline derivative, or a hole blocking material disclosed in JP No. 11-329734(A1), or BCP.

The thickness of the HBL may be in the range of about 50 to 1000 Å, and preferably, in the range of 100 to 300 Å. When the thickness of the HBL is less than 50 Å, the hole blocking ability of the HBL may be reduced. On the other hand, when the thickness of the HBL is greater than 1000 Å, the driving voltage of the device may increase.

Then, an electron transport layer (ETL) is formed by vacuum deposition, spin coating, casting, or the like. When the ETL is formed by vacuum deposition or spin coating, the conditions for deposition and coating are, in general, similar to those for the formation of the HIL, although the conditions for the deposition and coating conditions may vary according to the material that is used to form the ETL. The ETL may be formed of a quinoline derivative which stably transports injected electrons from a cathode, in particular, tris(8-quinolinorate)aluminum (Alq3), TAZ, or the like, which is known in the art.

The thickness of the ETL may be in the range of about 100 to 1000 Å, and preferably, 200 to 500 Å. When the thickness of the ETL is less than 100 Å, the electron transporting ability of the ETL may be reduced. On the other hand, when the thickness of the ETL is greater than 1000 Å, the driving voltage of the device may increase.

Then, an electron injection layer (EIL), which is formed of a material allowing easy injection of electrons from a cathode, can be formed on the ETL. The material that is used to form the EIL is not limited.

The EIL may be formed of LiF, NaCl, CsF, Li$_2$O, BaO, or the like, which is known in the art. Conditions for the deposition of the EIL are, in general, similar to conditions for the formation of the HIL, although they may vary according to the material that is used to form the EIL.

The thickness of the EIL may be in the range of about 1 to 100 Å, and preferably, 5 to 50 Å. When the thickness of the EIL is less than 1 Å, the electron injecting ability of the EIL may be reduced. On the other hand, when the thickness of the EIL is greater than 100 Å, the driving voltage of the device may increase.

Finally, a second electrode can be formed on the EIL by vacuum deposition, sputtering, or the like. The second electrode can be used as a cathode. The second electrode may be formed of a low work-function metal, an alloy, an electrically conductive compound, or a combination of these. In detail, the second electrode may be formed of Li, Mg, Al, Al—Li, Ca, Mg—In, Mg—Ag, or the like. Alternatively, a transparent cathode formed of ITO or IZO can be used to produce a front surface light emitting device.

The organic light emitting device according to an embodiment of the present invention may have a structure including a first electrode, a hole injection layer (HIL), a hole transport layer (HTL), an emitting layer (EML), a hole blocking layer (HBL), an electron transport layer (ETL), an electron injection layer (EIL) and a second electrode illustrated in FIG. 1C. However, the structure of the organic light emitting device according to embodiments of the present invention may vary and the layers may be removed, if desired.

Hereinafter, the present invention will be described in greater detail with reference to the following examples. The following examples are for illustrative purposes only and are not intended to limit the scope of the invention.

Synthesis Example 1

Compound 3 was synthesized through Reaction Scheme 1 below.

Reaction Scheme 1

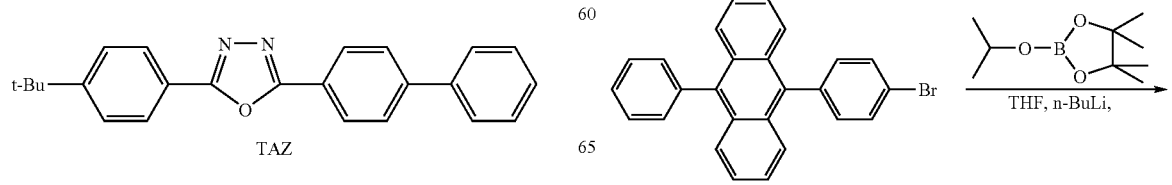

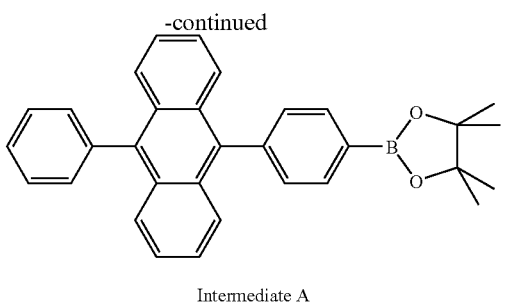

Intermediate A

Synthesis of Intermediate A

Synthesis of 4,4,5,5-Tetramethyl-2-[4-(10-phenyl-anthracen-9-yl)-phenyl]-[1,3,2]dioxaborolane (a)

4.6 g (11.2 mmol) of 9-(4-Bromo-phenyl)-10-phenyl-anthracene was dissolved in 150 ml of THF in a 500 ml round-bottom flask in an argon atmosphere, and 6.36 ml (15.9 mmol) of 2.5 M n-BuLi (in hexane) was added thereto at −78° C. Then, the flask was stirred at −78° C. for 1 hour and 3.52 ml (17.23 mmol) of 2-isopropoxy-4,4,5,5-tetramethyl-1,3,2-dioxabororane was added thereto, and then the flask was stirred at room temperature for 2 hours. 50 ml of water was added to the flask to terminate the reaction, and the mixture was subject to extraction using brine and methylene chloride. The extracted organic layer was dried using anhydrous magnesium sulfate, filtered, and the solvent was removed. The resultant was dissolved in a small amount of toluene, impurities were removed by column chromatography (silica and hexane), and polarity of an eluting solvent was increased to obtain 3.5 g (67%) of white solid.

Reaction Scheme 2

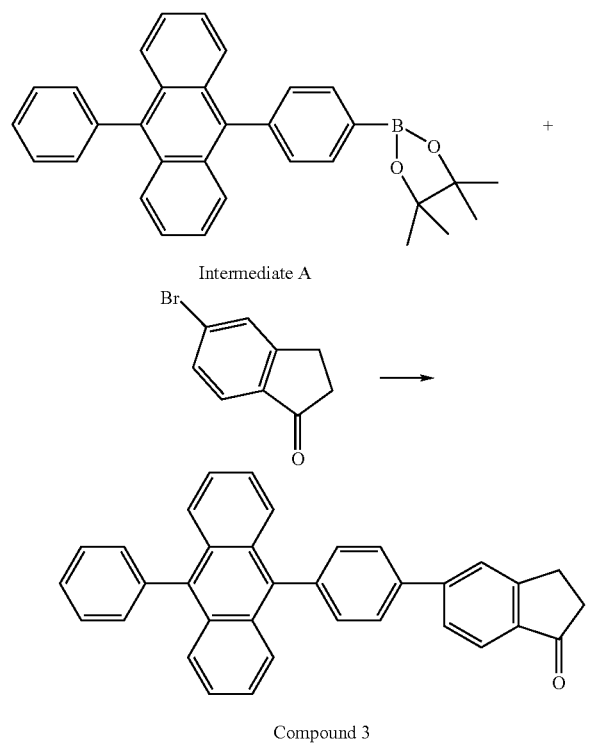

Compound 3

Synthesis of Compound 3

2.167 g (10.26 mmol) of Intermediate A was dissolved in 150 ml of THF and mixed with a solution in which 4.68 g (10.26 mmol) of 5-bromo-indan-1-one, 1.42 g (10.26 mmol) of tetrakis(triphenylphosphine)palladium(0) and 16 mmol of $K_2CO_3$ were dissolved in 70 ml of toluene and 8 ml of water. Then, the mixture was stirred at a refluxing temperature for 24 hours. When the mixture was cooled to room temperature, 200 ml of diethyl ether was added thereto. The resultant was washed twice with 300 ml of water to obtain an organic layer. The organic layer was dried with anhydrous magnesium sulfate to evaporate the solvent and a crude product was obtained. The crude product was separated and purified using silica gel column chromatography and recrystallized to obtain 2.1 g of Compound 3 (Yield: 88%).

The structure of the synthesized Compound 3 was identified by $^1$H NMR and LC-Mass.

1H-NMR (CDCl3, 300 MHz, ppm): 7.9-7.22 (m, 20H), 2.88 (s, 1H), 2.74 (s, 1H)

Evaluation Example 1

Evaluation of Emitting Properties

Emitting properties of film-shaped synthesized compounds were evaluated by measuring photoluminescence (PL) spectrum.

In order to evaluate optical properties of compounds of solution states, photoluminecscence (PL) spectrum of Compound 3 diluted in toluene to a concentration of 10 mM was measured using ISC PC1 spectrofluorometer equipped with a Xenon lamp. PL spectra of Compounds 3, 6 and 8 were repeatedly measured, and the results were shown in Table 1.

In addition, in order to evaluate optical properties of film-shaped compounds, a quartz substrate was washed with acetone and deionized water. Then, Compound 3 was spin coated on the substrate, heat-treated at 110° C. for 30 minutes to form a film having a thickness of 1000 Å. PL spectrum of the film was measured. PL spectra of Compounds 3, 6 and 8 were repeatedly measured, and the results are shown in Table 2 below.

TABLE 1

| Compounds | Maximum absorption wavelength (nm) | Maximum PL wavelength (nm) |
| --- | --- | --- |
| Compound 3 | 375, 397 | 414, 433 |
| Compound 6 | 378, 398 | 420, 440 |
| Compound 8 | 376, 397 | 418, 437 |

TABLE 2

| Compounds | Maximum absorption wavelength (nm) | Maximum PL wavelength (nm) |
| --- | --- | --- |
| Compound 3 | 378, 400 | 443 |
| Compound 6 | 381, 401 | 445 |
| Compound 8 | 380, 400 | 445 |

Referring to the results shown in Tables 1 and 2, the material according to the present invention has emitting properties suitably applied to an organic light emitting device.

Example 1

An organic light emitting device having a structure of ITO(1000 Å)/(M-TDATA) (35 nm)/α-NPD(30 nm)/(95% by weight of the compound of the present invention/5% by weight of DPAVBi)(35 nm)/ALq3(18 nm)/LiF(0.7 nm)/Al (150 nm) was prepared using the synthesized Compound as a host and DPAVBi as a dopant of an emitting layer.

15 Ω/cm² (1000 Å) ITO glass substrate was cut into pieces into 50 mm×50 mm×0.7 mm in size, followed by ultrasonic cleaning in isopropyl alcohol and deionized water for 15 minutes for each and then UV ozone cleaned for 30 minutes to produce an anode. M-TDATA was deposited on the substrate to a thickness of 35 nm, and α-NPD was vacuum deposited thereon to a thickness of 30 nm. Then, the compound according to the present invention and DPAVBi were vacuum deposited at the same time in a weight ratio of 95:5 to form an emitting layer with a thickness of 35 nm. Then, ALq3 was vacuum deposited on the emitting layer to form an electron transport layer with a thickness of 18 nm. LiF was vacuum deposited on the electron transport layer to form an electron injection layer with a thickness of 0.7 nm and Al was deposited on the electron injection layer to form a cathode with a thickness of 150 nm. As a result, an organic light emitting device having a structure shown in FIG. 1B was prepared. Emitting properties of the organic light emitting device were shown in Table 3 below.

Comparative Example 1

An organic light emitting device was prepared in the same manner as in Example 1, except that only DPAVBi was used as an emitting material instead of using the compound according to the present invention, and emitting properties of the organic light emitting device was shown in Table 3.

TABLE 3

| Compounds | Driving voltage (V) | Maximum current efficiency (cd/A) | CIE color coordinates (~100 cd/m$^2$) |
|---|---|---|---|
| Comparative Example 1 (DPAVBi) | 4.5 | 5.75 | (0.15, 0.23) |
| Compound 3 | 3.8 | 6.75 | (0.14, 0.20) |
| Compound 6 | 3.6 | 7.31 | (0.15, 0.21) |
| Compound 8 | 3.7 | 7.61 | (0.15, 0.21) |

According to the results obtained from the example and comparative example, it can be seen that an organic light emitting device including an emitting layer prepared using a compound according to the present invention, as a phosphorescent and fluorescent material, has excellent EL properties.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. An indene derivative compound represented by Formula 1 below:

X—Ar$_1$—Ar$_2$—Y     Formula 1 wherein the Ar$_1$ is selected from the group consisting of:

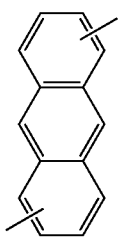
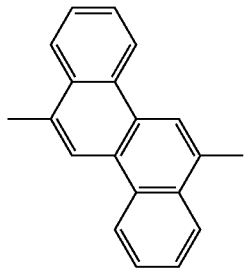
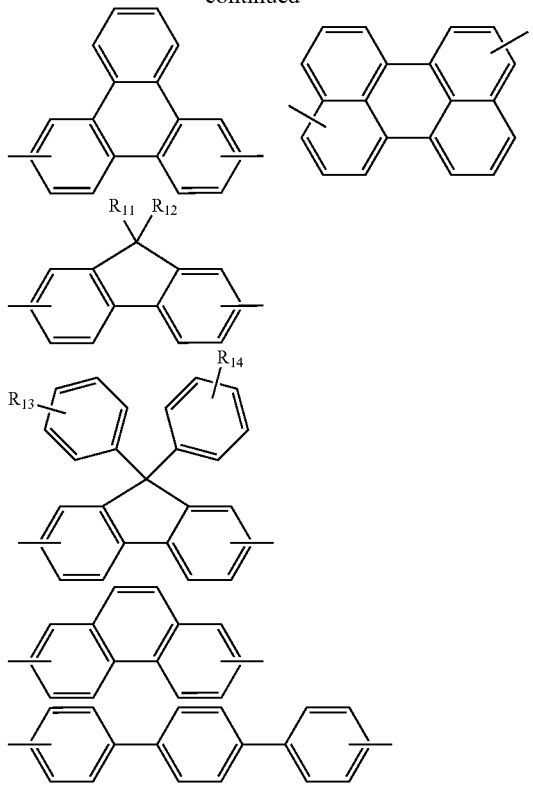
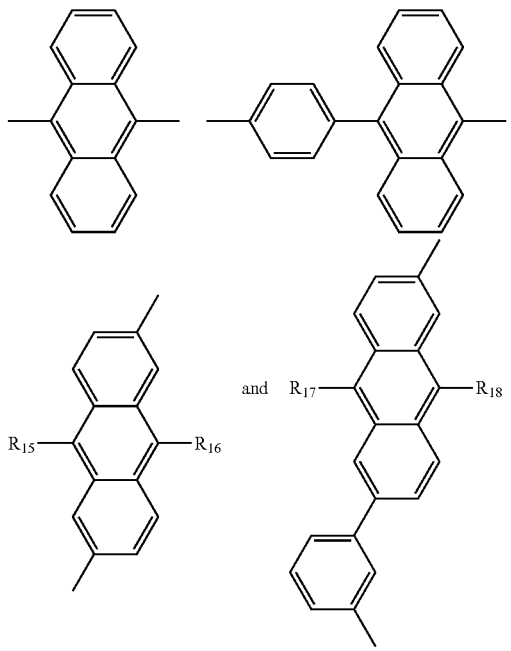

wherein R$_{11}$, R$_{12}$, R$_{13}$, R$_{14}$, R$_{15}$, R$_{16}$, R$_{17}$ and R$_{18}$ are each independently selected from the group consisting of a hydrogen atom, a substituted or unsubstituted C$_1$-C$_{20}$ alkyl group, a substituted or unsubstituted C$_6$-C$_{30}$ aryl group, a substituted or unsubstituted C$_2$-C$_{30}$ heteroaryl group, a substituted or unsubstituted C$_5$-C$_{20}$ cycloalkyl group and a substituted or unsubstituted C$_5$-C$_{30}$ heterocycloalkyl group, Ar₂ is selected from the group consisting of a substituted or unsubstituted $C_6$-$C_{15}$ arylene group, a substituted or unsubstituted $C_5$-$C_{15}$ heteroarylene group, a substituted or unsubstituted $C_5$-$C_{15}$ alkenylene group and a combination of at least two of them which are connected by a single bond, X is selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group, a substituted or unsubstituted $C_3$-$C_{30}$ arylsilane group and a group represented by one of Formulae 2a through 2d, and Y is a group represented by one of Formulae 2a through 2d:

Formula 2a

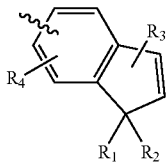

Formula 2b

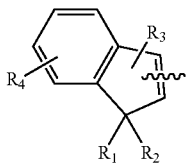

Formula 2c

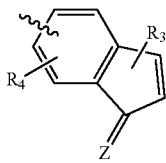

Formula 2d

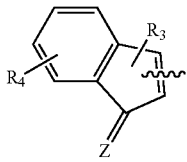

wherein $R_1$ to $R_4$ are each independently selected from the group consisting of a hydrogen atom, a halogen atom, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{30}$ arylamino group and a substituted or unsubstituted $C_3$-$C_{30}$ arylsilane group, and Z is O or S.

2. The indene derivative compound of claim 1, wherein the Ar₂ is selected from the group consisting of

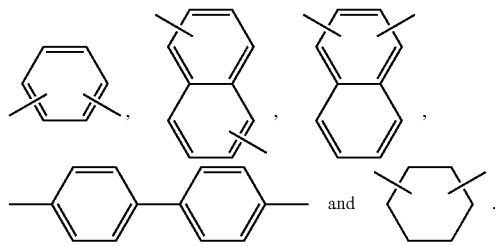

3. The indene derivative compound of claim 1, wherein the $R_1$ to $R_4$ and X are each independently a hydrogen atom, a $C_1$-$C_{50}$ alkyl group, a $C_1$-$C_{50}$ alkoxy group, a phenyl group, a biphenyl group, a petalenyl group, an indenyl group, a naphthyl group, a biphenylenyl group, an anthracenyl group, an azulenyl group, a heptalenyl group, an acenaphthylenyl group, a phenalenyl group, a fluorenyl group, a methylanthryl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a fluorenyl group, a pyranthrenyl group, an ovalenyl group, a carbazolyl group, a thiophenyl group, an indolyl group, a purinyl group, a benzimidazolyl group, a quinolinyl group, a benzothiophenyl group, a parathiazinyl group, a pyrrolyl group, a pyrazolyl group, an imidazolyl group, an imidazolinyl group, an oxazolyl group, a thiazolyl group, a triazolyl group, a tetrazolyl group, an oxadiazolyl group, a pyridinyl group, a pyridazinyl group, a pyrimidinyl group, a pyrazinyl group, a thianthrenyl group, a cyclopentyl group, a cyclohexyl group, an oxyranyl group, a pyrrolidinyl group, a pyrazolidinyl group, an imidazolidinyl group, a piperidinyl group, a piperazinyl group, a morpholinyl group, a di($C_6$-$C_{50}$ aryl)amino group, a tri($C_6$-$C_{50}$ aryl)silyl group and derivatives thereof.

4. The indene derivative compound of claim 1, being represented by one of Formulae 3 to 24 below:

Formula 3

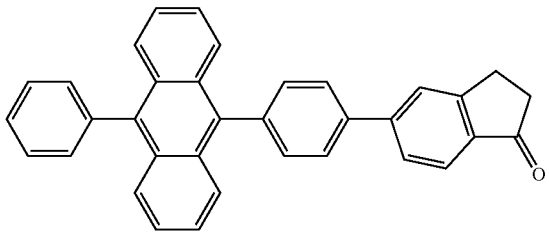

Formula 4

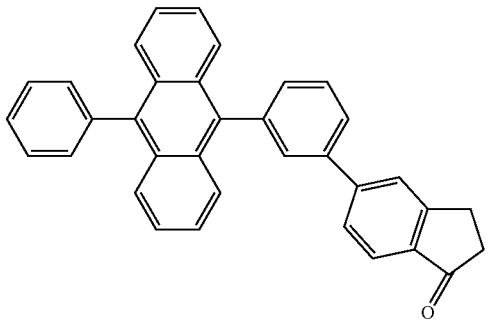

Formula 5
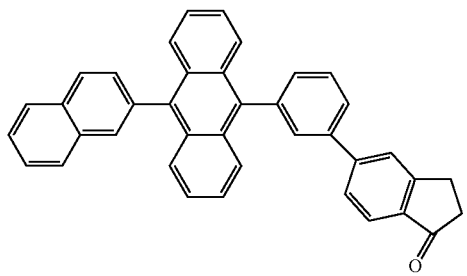
Formula 6
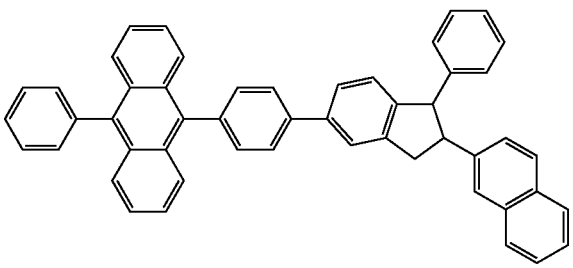
Formula 7
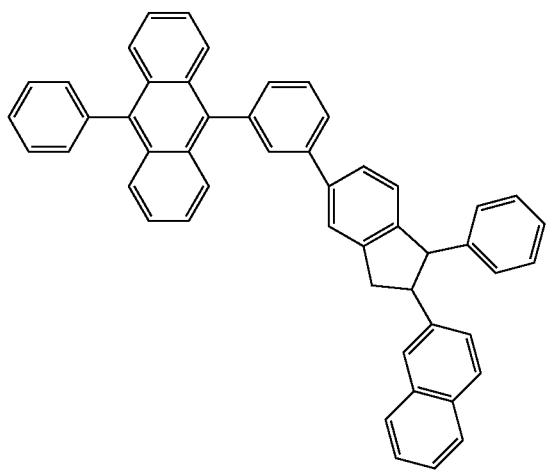
Formula 8
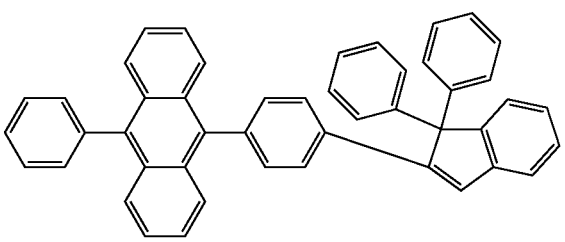
Formula 9
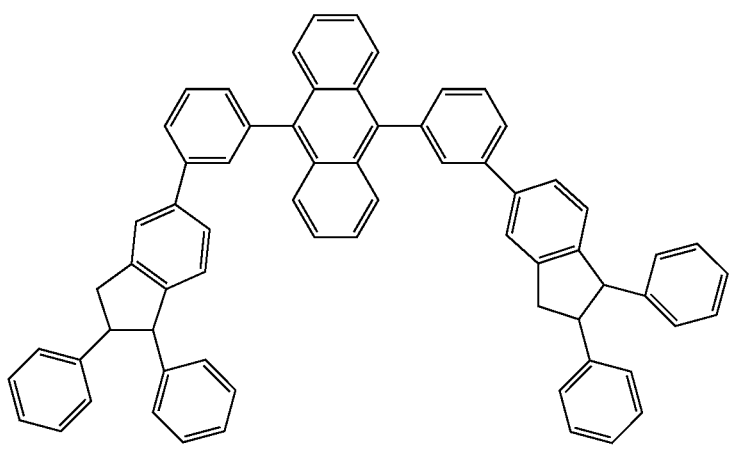
Formula 10
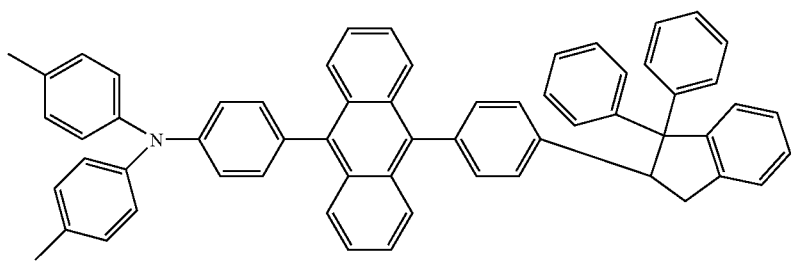

-continued
Formula 11
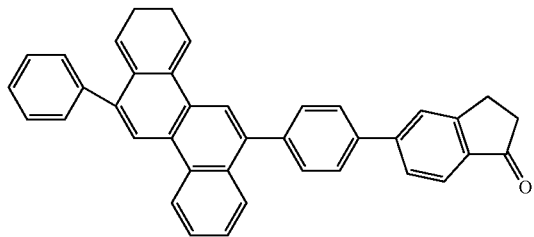
Formula 12
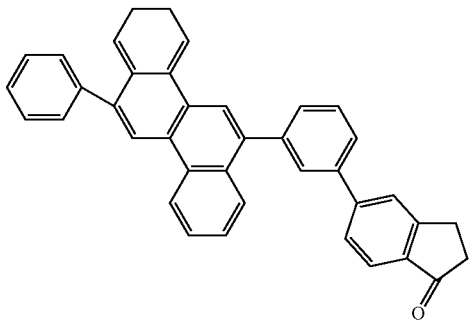
Formula 13
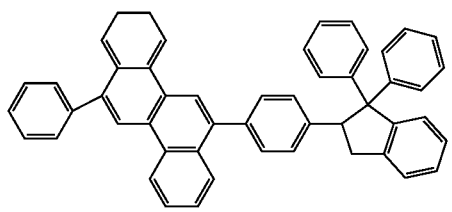
Formula 14
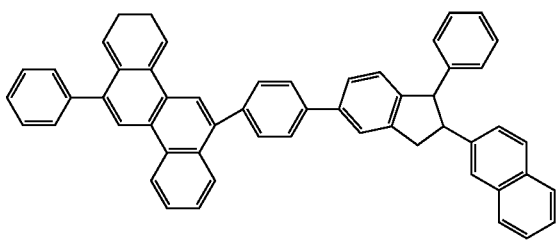
Formula 15
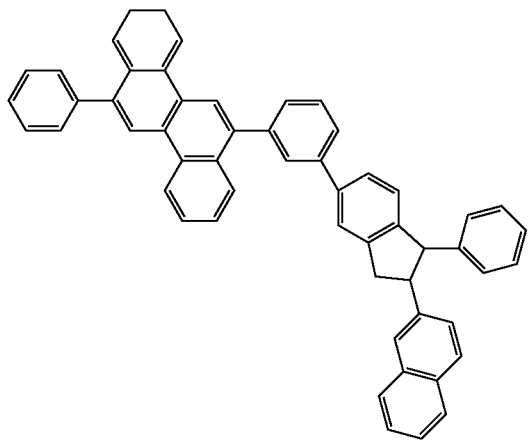
Formula 16
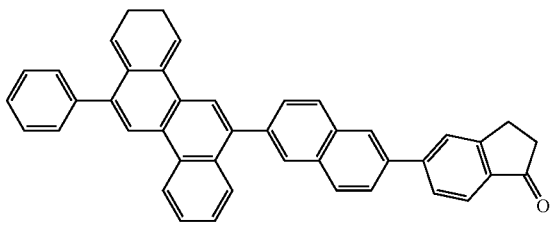
Formula 17
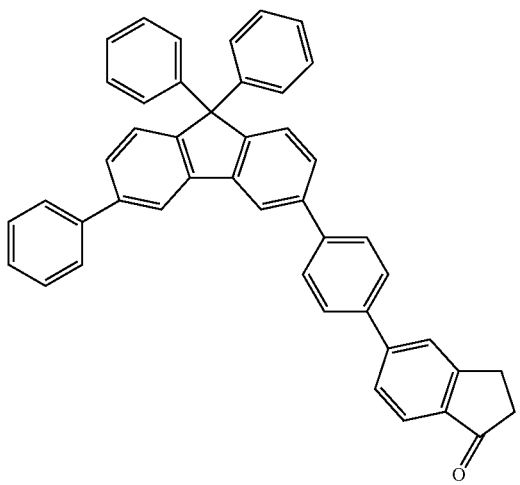
Formula 18
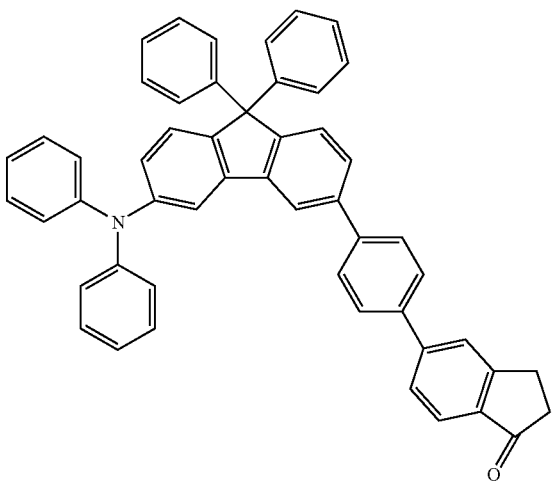

Formula 19
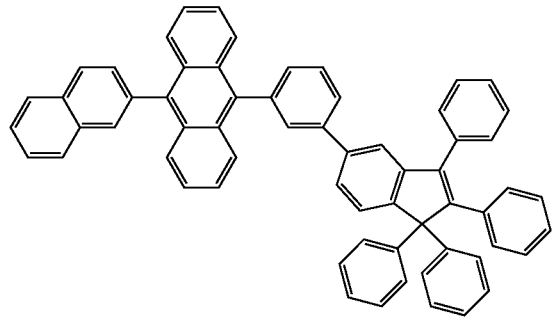
Formula 20
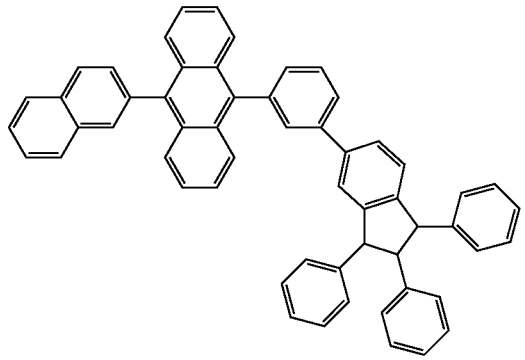
Formula 21
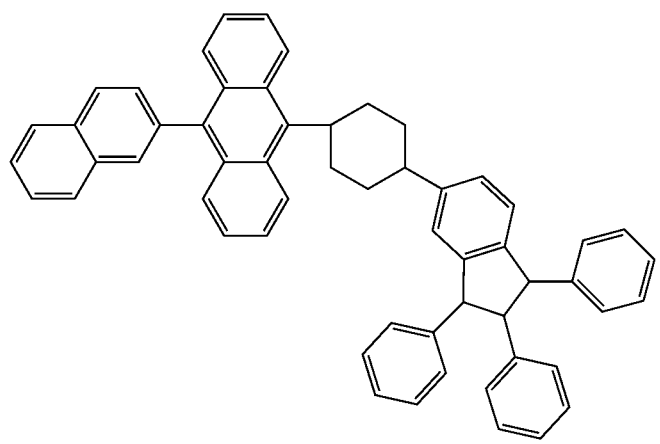
Formula 22
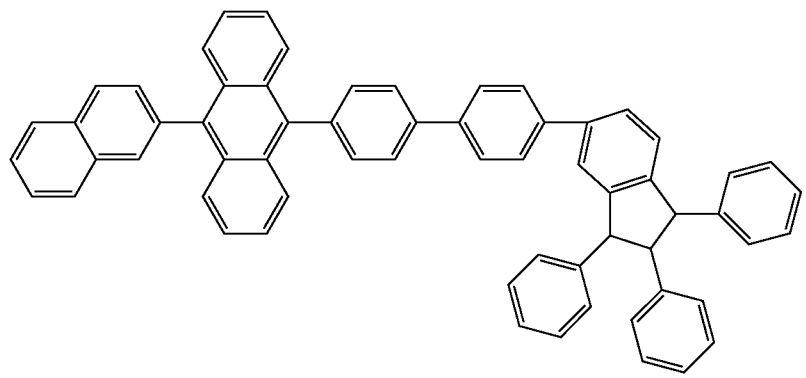

Formula 23

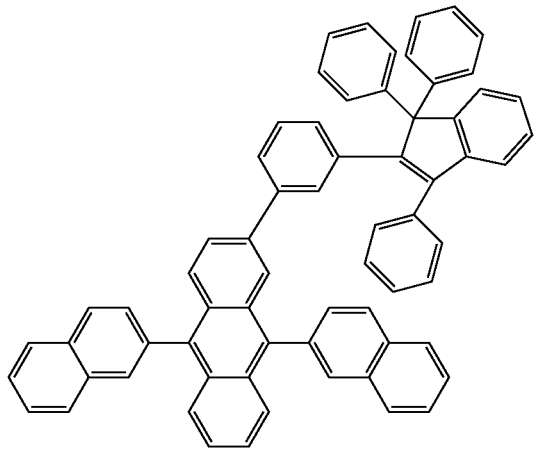

Formula 24

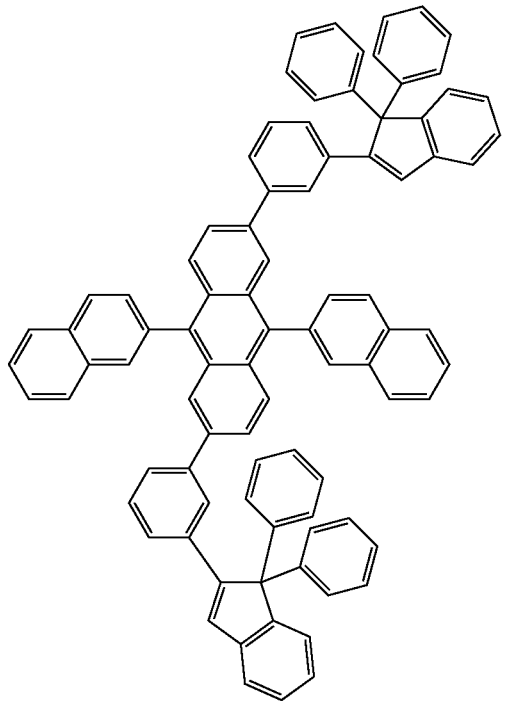

5. An organic light emitting device comprising: a first electrode; a second electrode; and at least one organic layer interposed between the first electrode and the second electrode, wherein the organic layer comprises an indene derivative compound according to claim 1.

6. An organic light emitting device comprising: a first electrode; a second electrode; and at least one organic layer interposed between the first electrode and the second electrode, wherein the organic layer comprises an indene derivative compound according to claim 2.

7. An organic light emitting device comprising: a first electrode; a second electrode; and at least one organic layer interposed between the first electrode and the second electrode, wherein the organic layer comprises an indene derivative compound according to claim 3.

8. An organic light emitting device comprising: a first electrode; a second electrode; and at least one organic layer interposed between the first electrode and the second electrode, wherein the organic layer comprises an indene derivative compound according to claim 4.

9. The organic light emitting device of claim 5, wherein the organic layer is selected from the group consisting of a hole injection layer, a hole transport layer, an electron blocking layer, an emitting layer, a hole blocking layer, an electron transport layer and an electron injection layer.

10. The organic light emitting device of claim 6, wherein the organic layer is selected from the group consisting of a hole injection layer, a hole transport layer, an electron blocking layer, an emitting layer, a hole blocking layer, an electron transport layer and an electron injection layer.

11. The organic light emitting device of claim 7, wherein the organic layer is selected from the group consisting of a hole injection layer, a hole transport layer, an electron blocking layer, an emitting layer, a hole blocking layer, an electron transport layer and an electron injection layer.

12. The organic light emitting device of claim 8, wherein the organic layer is selected from the group consisting of a hole injection layer, a hole transport layer, an electron blocking layer, an emitting layer, a hole blocking layer, an electron transport layer and an electron injection layer.

13. The organic light emitting device of claim 5, further comprising at least one layer selected from the group consisting of a hole injection layer, a hole transport layer, an electron blocking layer, a hole blocking layer, an electron transport layer and an electron injection layer between the first electrode and the second electrode.

14. The organic light emitting device of claim 9, wherein when the organic layer is an emitting layer, the emitting layer further comprises a phosphorescent or fluorescent dopant for red, green, blue or white color.

15. The organic light emitting device of claim 14, wherein the phosphorescent dopant is an organic metal compound comprising at least one element selected from the group consisting of Ir, Pt, Os, Ti, Zr, Hf, Eu, Tb and Tm.

16. The organic light emitting device of claim 13, comprising a structure selected from the group consisting of first electrode/hole injection layer/emitting layer/electron transport layer/electron injection layer/second electrode, first electrode/hole injection layer/hole transport layer/emitting layer/electron transport layer/electron injection layer/second electrode and first electrode/hole injection layer/hole transport layer/emitting layer/hole blocking layer/electron transport layer/electron injection layer/second electrode.

17. The indene derivative of claim 1, with a structure as follows:

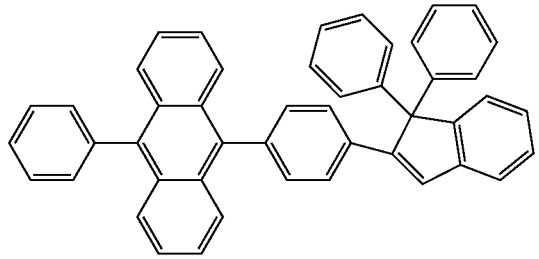

wherein in formula 1 of claim 1 $Ar_1$ is unsubstituted $C_{14}$ arylene;

$Ar_2$ is unsubstituted $C_6$ arylene;
X is unsubstituted $C_6$ aryl; and
Y is a group represented by Formula 2b:

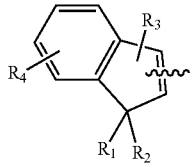 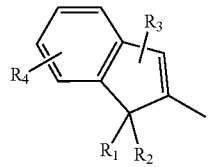

wherein $R_1$ is unsubstituted C6 aryl,
R2 is unsubstituted C6 aryl,
R3 is hydrogen, and
R4 is hydrogen.

* * * * *